US006221398B1

(12) United States Patent
Jakupovic et al.

(10) Patent No.: US 6,221,398 B1
(45) Date of Patent: *Apr. 24, 2001

(54) PROCESS FOR THE PREPARATION OF RESPIRABLE PARTICLES

(75) Inventors: Edib Jakupovic, Nykvarn; Jan Trofast, Lund, both of (SE)

(73) Assignee: Astra Aktiebolag, Sodertalje (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/669,477

(22) PCT Filed: Apr. 12, 1996

(86) PCT No.: PCT/SE96/00479

§ 371 Date: Jul. 10, 1996

§ 102(e) Date: Jul. 10, 1996

(87) PCT Pub. No.: WO96/32095

PCT Pub. Date: Oct. 17, 1996

(30) Foreign Application Priority Data

Apr. 13, 1995 (SE) .................................................. 9501384

(51) Int. Cl.[7] ................................ A61K 9/14; A61K 9/16

(52) U.S. Cl. ........................... 424/489; 424/499; 514/951

(58) Field of Search .................................... 424/489, 492, 424/497, 499; 514/951

(56) References Cited

U.S. PATENT DOCUMENTS

| | | | |
|---|---|---|---|
| 4,997,454 | * | 3/1991 | Violante et al. . |
| 5,254,330 | * | 10/1993 | Ganderton et al. . |
| 5,314,506 | * | 5/1994 | Midler, Jr. et al. . |
| 5,709,884 | * | 1/1998 | Trofast et al. . |

FOREIGN PATENT DOCUMENTS

| | | | |
|---|---|---|---|
| 0 169 618 A3 | * | 1/1986 | (EP) . |
| 0 169 618 A2 | | 1/1986 | (EP) . |
| 90/03782 | * | 4/1990 | (WO) . |
| 96/32095 | | 10/1996 | (WO) . |

OTHER PUBLICATIONS

Lewis W. Dittert, Ph.D., "An Introduction to Pharmaceutical Techniques and Dosage Forms", 1991, J.B. Lippincott Company, Seventh Edition, Taiwan.

Herbert A. Lieberman et al., "Disperse Systems", 1988, Marcel Dekker, Inc., vol. I, New York.

* cited by examiner

*Primary Examiner*—Thurman K. Page
*Assistant Examiner*—Brian K. Seidleck
(74) *Attorney, Agent, or Firm*—Fish & Richardson P.C.

(57) ABSTRACT

A process for producing a pharmaceutical powder for inhalation comprising crystalline particles of an inhalation compound, comprising dissolving an inhalation compound in a solvent; and introducing the solution containing the inhalation compound in droplet form or as a jet stream into an anti-solvent which is miscible with the solvent and which is under agitation.

23 Claims, No Drawings

PROCESS FOR THE PREPARATION OF RESPIRABLE PARTICLES

This application is a 371 of PCT SE96/00479, filed Apr. 12, 1996.

FIELD OF THE INVENTION

This invention relates to a process for preparing a pharmaceutical powder for inhalation, which powder comprises crystalline particles of an inhalation compound, in particular particles of mass median diameter 10 μm or less.

BACKGROUND OF THE INVENTION

Inhalation of dry powders has been recognized as a valuable method for the administration of pharmacological agents and in particular those which are useful in the treatment of diseases of the respiratory tract. However, the utility of the method has been limited by the difficulty in making appropriate doses available to the lower respiratory tract of the patient. In general only a relatively small proportion of any nominal dose will reach the lower respiratory tract of the inhaling patient; the remainder may remain in the inhaler device or be deposited in the mouth and throat of the patient.

One major factor determining the proportion of inhalable drug which will reach the lower respiratory tract of a patient is the particle size distribution of the particles emerging from the inhaler device. This particle size distribution is in turn dependent both on the construction and function of the inhaler, and the powder fomuation. The present application is concerned with the nature of the powder formulation. This should have a high integrity of the crystal structure, or crystal habit (as may be measured using X-ray crystallography techniques, for example), high purity and stability, and a particle size within the respirable particle range.

In order to achieve a desired crystal structure and particle sum powder formulations of respirable particles are in general obtained by processes including crytallization from solution followed by micronization However, optimum crystal structure formation and optimum purity may not be obtained in this process, and micronization has associated problems. Prolonged comminution rests in a high energy powder and crystal lattice defects which may be manifested for example in lower stability, and/or hygroscopicity. As micronization results in some amorphous character on the surface of the obtained particles, a "conditioning" step is necessary in order to obtain a particle considered to be completely crystalline. International patent applications PCT/SE91/00186 (WO 92/18110) and PCT/SE94/00780 (WO 95/05805) describe methods of conditioning substances in order to obtain crystalline products. It is an object of the present invention to provide a process for the production of crystalline respirable particles which avoids the necessity for post-crystallisation micronization.

European Patent No. 437451 discloses a process for producing finely divided solid crystalline powders, comprising dissolving the solid to be finely divided in a liquid carrier solvent to form an injection solution and adding the injection solution to a volume of anti-solvent, which is a supercritical fluid, liquefied compressed gas or dense vapour, sufficient to precipitate or crystallise the solid.

European patent application, publication number 0 542 314 A1, discloses a method of forming microparticles of a material, involving bringing a supercritical anti-solvent gas into contact with a solution of said material in a solvent at a controlled rate operable to expand the solution and precipitate the material. Needles and globules are formed.

Neither of the above are directed to powders for inhalation per se, and as they use supercritical media the use of compressed gases and heavy, expensive apparatus is necessitated.

U.S. Pat. No. 5,314,506, again not related to powders for inhalation, describes impinging a jet stream of an organic pharmaceutical compound and a jet stream of an anti-solvent, to precipitate small crystals of the organic pharmaceutical compound. Pressurised blow-cans and elevated temperatures are employed, and the crystals obtained range from flakes of up to 25 microns, to needles, and cubes of less than 3 microns.

EP 0169618 discloses a method for the preparation of water-insoluble organic compounds such as may be used in suspensions for intravenous injection, as non-crystalline particles. The method involves preparing a solution of the compound in a water-miscible organic solvent and infusing an aqueous precipitating liquid into the organic solution, in most cases in the presence of surfactant.

The process of the present invention aims to provide a powder for inhalation comprising crystalline particles of an inhalation compound of mass median diameter less than 10 μm, irrespective of the substance concerned. Thus the process does not require the use of supercritical media nor the processes of micronizing and conditioning.

According to the present invention there is provided a process for producing a pharmaceutical powder for inhalation comprising crystalline particles of an inhalation compound, comprising dissolving an inhalation compound to be provided in crystalline particle form in a solvent; and introducing the solution containing the inhalation compound, in droplet form or as a jet stream into an anti-solvent which is miscible with the solvent and which is under agitation, under non-supercritical conditions.

There is also provided according to the present invention a pharmaceutical powder and a crystalline inhalation compound obtainable by the process of the invention.

Preferably the particles of the inhalation compound of the present invention have a mass median diameter of at least 0.1 μm, more preferably at least 1 μm. Where the powder is intended particularly for oral inhalation, preferably the particles have a mass median diameter of 10 μm or less, preferably 7 μm or less. Most preferably the particles have a mass median diameter of 1–6 μm. By "mass median diameter" is meant that half of the mass of the inhalation compound is made up of particles having a diameter less than the mass median diameter and half of the mass of the inhalation compound is made up of particles having a diameter greater than the mass median diameter. Preferably as much as possible of the powder consists of particles of diameter 10 μm or less; for example at least 75% or at least 90% of the powder consists of particles of diameter 10 μm or less.

The pharmaceutical powder of the present invention may be administered orally or nasally. Where nasal administration is intended the particles of the inhalation compound may have a mass median diameter outside the above preferred ranges.

The pharmaceutical powder may comprise a water-soluble inhalation compound, or a water-insoluble inhalation compound.

The solution containing the inhalation compound is introduced into the anti-solvent in droplet form or as a jet-stream, for example through a porous filter or one or more nozzles.

Through the present invention it is possible to control the size of particles obtained by controlling any or all of parameters such as the concentration of the compound in the solvent, the rate of addition of the solution into the anti-solvent and the intensity of the agitation such that particles within a specific desired particle size range may be obtained. A powder formulation having good physicochemical stability and needing no mechanical micronization or conditioning is obtained.

Medically useful compounds which may be provided in respirable particle form according to the present invention include β2-adrenoteceptor agonists, for example salbutamol, terbutaline, rimiterol, fenoterol, reproterol, adrenaline, pirbuterol, isoprenaline, orciprenaline, bitolterol, salmeterol, formoterol, clenbuterol procaterol, broxaterol, picumeterol, TA-2005 ([8-hydroxy-5-(1-hydroxy-2-((2-(4-methoxyphenyl)-1-methylethyl)amino)ethyl)]-2(1H) quinolone), mabuterol; anticholineigic bronchodilators, for example ipratropium bromide; glucocorticosteroids, for example betamethasone, fluticasone, budesonide, tipredane, dexamethasone, beclomethasone, fluocinolone, triamcinolone acetonide, mometasone and rofleponide; peptides and proteins, for example insulin, immunomodulators, anti-allergic drugs for example sodium cromoglycate and nedocromil sodium; expectorants; mucolytics; antihistamines; cyclooxygenase inhibitors; leukotriene synthesis inhibitors; leukotiene antagonists, PLA2 inhibitors, PKC-inhibitors, PAF antagonists and prophylactics of asthma; or pharmacologically acceptable esters and salts and/or solvates thereof. For example salbutamol and terbutaline may be used as the sulphate; fenoterol as the hydrobromide; salmeterol as the xinafoate; formoterol as the fumarate dihydrate; clenbuterol as the hydrochloride; fluticasone as the propionate; and broxaterol as the monohydrochloride.

Preferably the medically useful compound is selected from β2-adrenoreceptor agonists and glucocorticosteroids.

Most preferably the medically useful compound is selected from salbutamol, preferably as the sulphate, salmeterol, preferably as the xinafoate, formoterol, preferably as the fumarate dihydrate, budesonide, terbutaline, preferably as the sulphate, fluticasone, preferably as the propionate, rofleponide, preferably as the palmitate, and other pharmaceutically acceptable esters and salts and/or solvates thereof Pharmaceutically acceptable additives e.g., carriers, diluents, and penetration enhancers may also be prepared according to the present invention. For example the process of the present invention may be used to prepare carbohydrates such as lactose, dextrose, melezitose, maltose, mannitol, trehalose and raffinose, as well as salts of fatty acids, bile salts, phospholipids and alkyl glycosides, which may be useful as penetration enhancers. The pharmaceutically acceptable additive may be prepared stately from the medically useful compound, and the powders may then be mixed together, or a powder containing the medically useful compound and additive may be prepared in certain cases, i.e. when the compound and additive have similar solubilities, by dissolving all of the desired substances together in the solvent according to the present invention.

In the process of the present invention, the choice of solvent depends upon the solubility of the compound to be dissolved. Preferably, a substantially saturated or supersaturated solution is obtained. The anti-solvent should be miscible with the solvent in order that a single-phase solvent mixture is formed and should be such that the dissolved compound is precipitated immediately upon contact therewith.

The choice of particular solvent and anti-solvent can be made readily by a person skilled in the art considering the solubility characteristics of the compound to be precipitated. In general, water-soluble substances may be dissolved in water or another solvent more polar than the anti-solvent, or a mixture of such solvents, and precipitated with a less polar solvent (the anti-solvent); and substantially water-insoluble substances may be dissolved in a less polar solvent and precipitated with water or another "more polar" solvent (the anti-solvent). For example, a water-soluble substance which is dissolved for example in water may be precipitated with an anti-solvent such as ethyl acetate, acetone, methylethyl ketone (2-butanone), isopropanol, or mixtures of for example 10–20% methanol, isopropanol or ethanol with 80–90% (w/w) methylethyl ketone or isopropanol, while a less water-soluble substance may be dissolved for example in an organic solvent such as methanol, isopropanol or another alcohol, dimethyl sulphoxide, dimethyl formamide, N'N'-dimethyl acetamide or phenol and precipitated with for example water.

To maximize the degree of precipitation it is desirable that the solution is added to the anti-solvent at temper as low as possible, but low temperatures are not essential for the process of the present invention. Preferably, the solution is added to the anti-solvent at temperatures of below 25° C., for example at around 0° C. or from 0 to 5° C.

According to the present invention the solution is preferably added to the anti-solvent though a porous filter having pores of 10–160 microns, such as Pyrex Glass Filters of porosity grades 1–4.

The rate of addition may be controlled, for example by using a pump, such as a peristaltic pump when working on a laboratory scale.

In order that the droplet or fine jet, as well as the precipitated compound, is efficiently removed from the porous filter or nozzle, it is necessary for the anti-solvent to be under agitation. The agitation may be achieved in various ways such as by means of mechanical stirring with propellers, turbines, paddles, anchor impellers or Ystral equipment, or by using ultrasound waves on or beside the filter or nozzles.

The precipitated compound may be dried in conventional manner, for example it may be spray-dried, and may be agglomerated and/or spheronized if desired. No conditioning is necessary as the particles obtained are considered to be completely crystalline.

The size of the particles obtained according to the present process may be controlled by adjusting the process parameters, as will be evident to a person skilled in the art. For example, decreasing the concentration of compound in the solvent will lead to smaller particles, and adjusting the rate of addition and/or agitation will alter the particle size by altering the size of the droplet from which the compound is precipitated. Any one, several, or all of the process parameters may be adjusted in order to obtain a particular particle size range. The optimal process parameters in each case may be determined by a person skilled in the art using routine experimentation.

Various methods may be employed in order to monitor the crystallinity of the respirable particles of the present invention. Such methods, which are all well known to the skilled person in the art, include isothermal micro calorimetry, BET gas adsorption, X-ray powder diffraction and differential scanning calorimetry (DSC). For example during a recrystallization a large amount of heat is evolved and by monitoring the calometrical signal the sample may be checked for any amorphous content.

The following Examples are intended to illustrate, but not limit, the scope of the present invention. The particle sizes given were measured using a Malvern Master Sizer instrument.

EXAMPLE 1

A solution of budesonide (15 g) in methanol (300 ml) was added to water (450 ml) at a temperature of 0° C., through a glass filter, Pyrex porosity grade 3 (pore index 16–40 microns), and with stirring with ultraturrax equipment.

A slurry was obtained, containing particles with a mass median diameter (MMD) of 2.2 microns. 90% of the particles had a diameter of below 5.3 μm. The slurry was spray dried using a commercially available spray-dryer (Büchi 190), to give a budesonide powder consisting of particles of MMD 2.9 microns having no amorphous character, Le., crystalline particles, determined using powder X-ray measurements. 90%/ of the particles had a diameter of below 5.7 μm.

The particles obtained could be agglomerated for use in dry powder inhalers.

EXAMPLE 2

A solution of budesonide (2.35 g) in methanol (60 ml) was added to water/ice (200 ml) at a rate of 1 ml/min, through a glass filter with a porosity of 40–90 microns, and with stirring with ultraturrax equipment (4.5). The obtained slurry contained budesonide crystalline particles of MMD 2.79 microns. 90% of the particles had a diameter of below 6.0 μm.

EXAMPLE 3

A solution of budesonide (1.5 g) in methanol (80 ml) was added to waterrice (300 ml) at a rate of 1 ml/min, through a Pyrex glass filter of porosity grade 2 (40–100 microns), and with stirring with ultraturrax equipment (4.5). The obtained slurry contained budesonide crystalline particles of MMD 2.60 microns. 90% of the particles had a diameter of below 6.0 μm.

EXAMPLE 4

The procedure of Example 3 was repeated using a Pyrex glass filter of porosity grade 4 (10–16 microns). The obtained slurry contained budesonide crystalline particles of MMD 2.49 microns. 90% of the particles had a diameter of below 6.0 μm.

EXAMPLE 5

A solution of budesonide (3 g) in methanol (90 ml) was added to water/ice (300 ml) at a rate of 1 ml/min, through a Pyrex glass filter of porosity grade 1 (100–160 microns), and with stirring with ultraturrax equipment (4.5). The obtained slurry contained budesonide crystalline particles of MMD 4.76 microns. 90% of the particles had a diameter of below 9.6 μm.

EXAMPLE 6

A solution of budesonide (1.2 g) in methanol (50 ml) was added via a peristaltic pump and through a glass filter, Pyrex no. 3 (16–40 microns), to water (200 ml) at 0° C. and with stirring with Ystral agitation equipment. The rate of addition was 3 ml/min and the rate of stirring was 1500 r/min. The slurry obtained contained budesonide crystalline particles of MMD 4.2 microns. 90% of the particles had a diameter of below 8.6 μm.

EXAMPLE 7

A solution of lactose (2.0 g) in water was added via a peristaltic pump and through a glass filter, Pyrex no. 3, to a 20% solution of ethanol in methylethyl ketone, with stirring with Ystral agitation equipment. The rate of addition was 3 ml/min and the rate of stirring was 1500 r/min. The slurry obtained contained lactose particles of MMD 5.2 microns. 75% of the particles had a diameter of below 10.0 μm.

EXAMPLE 8

A solution of salbutamol sulphate (1 g) in water (7 ml) was added via a peristaltic pump and through a glass filter, Pyrex no. 2, to a 20% solution of ethanol in methylethyl ketone at room temperature, with stirring with Ysral agitation equipment. The rate of addition was 3 ml/min and the rate of stirring was 1500 r/min. The slurry obtained contained salbutamol sulphate crystalline particles of MMD 5.2 microns. 75% of the particles had a diameter of below 10.0 μm.

What is claimed is:

1. A process for producing a pharmaceutical powder for inhalation, the powder comprising crystalline particles of an inhalation compound selected from the group consisting of salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, 8-hydroxy-5-(1-hydroxy-2-((2-(4-methoxyphenyl)-1-methylethyl)amino)ethyl)-2(1H)-quinoline, mabuterol, betamethasone, fluticasone, budesonide, tipredane, dexamethasone, beclomethasone, fluocinolone, trianicinolone, acetonide, mometasone, rofleponide, and pharmacologically acceptable esters, salts and solvates of these compounds, the particles having a mass median diameter (MMD) of 10 μm or less, the process comprising

- dissolving the inhalation compound in a solvent to form a solution; and
- introducing the solution containing the inhalation compound, in droplet form or as a jet stream, into an anti-solvent which is miscible with the solvent and which is under agitation, under non-supercritical conditions and at a temperature of less than 25° C., to form the crystalline particles having a MMD of 10 μm or less.

2. A process as claimed in claim 1 wherein the particles of the inhalation compound have a mass median diameter of 7 μm or less.

3. A process as claimed in claim 1 wherein the particles of the inhalation compound have a mass median diameter of at least 0.1 μm.

4. A process as claimed in claim 1 wherein the particles of the inhalation compound have a mass median diameter of at least 1 μm.

5. A process as claimed in claim 1 wherein the particles of the inhalation compound have a mass median diameter of 1–6 μm.

6. A process as claimed in claim 1 wherein at least 75% of the powder consists of particles having a diameter of 10 μm or less.

7. A process as claimed in claim 1 wherein at least 90% of the powder consists of particles having a diameter of 10 μm or less.

8. A process as claimed in claim 1 wherein the solution containing the inhalation compound is introduced into the anti-solvent through a porous filter.

9. A process as claimed in claim 1 wherein the solution containing the inhalation compound is introduced into the anti-solvent through one or more nozzles.

10. A process as claimed in claim 1 wherein the solution containing the inhalation compound is substantially saturated or supersaturated.

11. A process as claimed in claim 1 wherein the inhalation compound is salbutamol sulphate.

12. A process as claimed in claim 1 wherein the inhalation compound is formoterol fumarate dihydrate.

13. A process as claimed in claim 1 wherein the inhalation compound is budesonide.

14. A process as claimed in claim 1 wherein the inhalation compound is terbutaline sulphate.

15. A process as claimed in claim 1 wherein the inhalation compound is rofleponide palmitate.

16. A process as claimed in claim 1 wherein the inhalation compound is salmeterol xinafoate.

17. A process as claimed in claim 1 wherein the anti-solvent is selected from the group consisting of ethyl acetate, acetone, methylethyl ketone, isopropanol, and mixtures of 10–20% of a first solvent selected from the group consisting of methanol, isopropanol and ethanol with 80–90% of a second solvent selected from the group consisting of methylethylketone and isopropanol.

18. A process as claimed in claim 1 wherein the inhalation compound is substantially water-insoluble, the solvent is less polar than the anti-solvent, and the anti-solvent is water or another polar solvent or nature of polar solvents.

19. A process as claimed in claim 18 wherein the solvent is selected from methanol, isopropanol, dimethylsulphoxide, dimethylformamide, N'N'-dimethyl acetamide and phenol.

20. A process as claimed in claim 1 wherein the solution containing the inhalation compound is added to the anti-solvent at a temperature of from 0° C. to 5° C.

21. A process as claimed in claim 1 wherein agitation of the anti-solvent is achieved by means of mechanical sting, propellers, turbines paddles, anchor impellers or Ystral equipment, or by using ultrasound waves on or beside the filter or nozzles.

22. A pharmaceutical powder obtainable by the process of claim 1, consisting essentially of said crystalline particles having a MMD of 10 $\mu$m or less.

23. A pharmaceutical powder for inhalation comprising an inhalation compound obtainable by the process of claim 1, said pharmaceutical powder consisting essentially of particles having a MMD of 10 $\mu$m or less.

* * * * *